(12) United States Patent
Nadeau et al.

(10) Patent No.: US 6,656,680 B2
(45) Date of Patent: Dec. 2, 2003

(54) PROBES AND METHODS FOR DETECTION OF NUCLEIC ACIDS

(75) Inventors: James G. Nadeau, Ellicott City, MD (US); Tobin J. Hellyer, Owings Mills, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 181 days.

(21) Appl. No.: 09/894,788

(22) Filed: Jun. 28, 2001

(65) Prior Publication Data

US 2002/0094527 A1 Jul. 18, 2002

Related U.S. Application Data

(62) Division of application No. 09/590,061, filed on Jun. 8, 2000, now Pat. No. 6,316,200.

(51) Int. Cl.[7] .......................... C12Q 1/68; C07H 21/02; C07H 21/04; C12P 19/34
(52) U.S. Cl. ...................... 435/5; 536/23.1; 536/24.3; 435/91.2
(58) Field of Search ................. 536/23.1, 24.2, 536/24.3, 24.31, 24.32, 24.33, 25.3; 435/6, 91.1, 94

(56) References Cited

U.S. PATENT DOCUMENTS

| 5,270,184 | A | | 12/1993 | Walker et al. |
| 5,455,166 | A | | 10/1995 | Walker |
| 5,525,494 | A | * | 6/1996 | Newton ..................... 435/91.2 |
| 5,547,861 | A | | 8/1996 | Nadeau et al. |
| 5,550,025 | A | | 8/1996 | Walker |
| 5,593,867 | A | | 1/1997 | Walker et al. |
| 5,607,834 | A | | 3/1997 | Bagwell |
| 5,691,145 | A | | 11/1997 | Pitner et al. |
| 5,846,726 | A | | 12/1998 | Nadeau et al. |
| 5,866,336 | A | | 2/1999 | Nazarenko et al. |
| 5,928,869 | A | | 7/1999 | Nadeau et al. |

FOREIGN PATENT DOCUMENTS

| EP | 0684315 A1 | 11/1995 |
| JP | 93 015439 B | 1/1986 |

OTHER PUBLICATIONS

Tyagi, et al., 1996 Nature Biotechnology, vol. 14, 303–8.
Ghosh, Nucleic Acids Research, 1994, vol. 22, No. 15, 3155–59.
Lee, Nucleic Acids Research, 1993, vol. 21, No. 16, 3761–66.
Bagwell, Nucleic Acids Research, 1994, vol. 22, No. 12, 2424–25.

* cited by examiner

*Primary Examiner*—Ethan Whisenant
(74) *Attorney, Agent, or Firm*—Allan M. Kiang (57) ABSTRACT

The invention employs an unlabeled signal primer comprising a 5' adapter sequence for detection of nucleic acid target sequences. The detection system further comprises a reporter probe, the 3' end of which hybridizes to the complement of the 5' adapter sequence of the signal primer to produce a 5' overhang. Polymerase is used to fill in the overhang and synthesize the complement of the 5' overhang of the reporter probe. Synthesis of the reporter probe complement is detected, either directly or indirectly, as an indication of the presence of the target.

15 Claims, 5 Drawing Sheets

```
                        SEQUENCE LISTING

<160> NUMBER OF SEQ ID NOS: 20

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:Synthetic
      sequence for experimental model

<400> SEQUENCE: 1
ccaaaatgac agcttctgat ggaatgactc actgagttgg aacgt            45

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:Synthetic
      sequence for experimental model

<400> SEQUENCE: 2
tacctcgagt gcagccaaaa gacagcttct gatggaa                     37

<210> SEQ ID NO 3
<211> LENGTH: 48
<212> TYPE: DNA
<213> ORGANISM: Human immunodeficiency virus

<400> SEQUENCE: 3
gaaagacgtt agccaccata cggatacccc ttttctttta aaattgtg         48

<210> SEQ ID NO 4
<211> LENGTH: 52
<212> TYPE: DNA
<213> ORGANISM: Human immunodeficiency virus

<400> SEQUENCE: 4
gaaagacgtt agccaccata cggatacccc ttttctttta aaattgtgga tg    52

<210> SEQ ID NO 5
<211> LENGTH: 45
<212> TYPE: DNA
<213> ORGANISM: Human immunodeficiency virus
```

```
<400> SEQUENCE: 5
gaaagacgtt agccaccata cggatacccc ttttctttta aaatt                    45

<210> SEQ ID NO 6
<211> LENGTH: 46
<212> TYPE: DNA
<213> ORGANISM: Human immunodeficiency virus

<400> SEQUENCE: 6
gaaagacgtt agccaccata cggatacccc ttttctttta aaattg                   46

<210> SEQ ID NO 7
<211> LENGTH: 43
<212> TYPE: DNA
<213> ORGANISM: Human immunodeficiency virus

<400> SEQUENCE: 7
acgttagcca ccatacggat acccctttc ttttaaaatt gtg                      43

<210> SEQ ID NO 8
<211> LENGTH: 47
<212> TYPE: DNA
<213> ORGANISM: Human immunodeficiency virus

<400> SEQUENCE: 8
acgttagcca ccatacggat acccctttc ttttaaaatt gtggatg                  47

<210> SEQ ID NO 9
<211> LENGTH: 40
<212> TYPE: DNA
<213> ORGANISM: Human immunodeficiency virus

<400> SEQUENCE: 9
acgttagcca ccatacggat acccctttc ttttaaaatt                         40

<210> SEQ ID NO 10
<211> LENGTH: 41
<212> TYPE: DNA
<213> ORGANISM: Human immunodeficiency virus

<400> SEQUENCE: 10
acgttagcca ccatacggat acccctttc ttttaaaatt g                       41

<210> SEQ ID NO 11
<211> LENGTH: 38
<212> TYPE: DNA
<213> ORGANISM: Human immunodeficiency virus

<400> SEQUENCE: 11
agccaccata cggatacccc ttttctttta aaattgtg                            38

<210> SEQ ID NO 12
<211> LENGTH: 42
<212> TYPE: DNA
<213> ORGANISM: Human immunodeficiency virus

<400> SEQUENCE: 12
agccaccata cggatacccc ttttctttta aaattgtgga tg                       42

<210> SEQ ID NO 13
<211> LENGTH: 35
<212> TYPE: DNA
<213> ORGANISM: Human immunodeficiency virus
```

<400> SEQUENCE: 13
agccaccata cggataccccc ttttcttta aaatt                         35

<210> SEQ ID NO 14
<211> LENGTH: 36
<212> TYPE: DNA
<213> ORGANISM: Human immunodeficiency virus

<400> SEQUENCE: 14
agccaccata cggataccccc ttttcttta aaattg                        36

<210> SEQ ID NO 15
<211> LENGTH: 34
<212> TYPE: DNA
<213> ORGANISM: Human immunodeficiency virus

<400> SEQUENCE: 15
tgcccgagtg aaagacgtta gccaccatac ggat                          34

<210> SEQ ID NO 16
<211> LENGTH: 40
<212> TYPE: DNA
<213> ORGANISM: Human immunodeficiency virus

<400> SEQUENCE: 16
tagtgcccga gcactgaaag acgttagcca ccatacggat                    40

<210> SEQ ID NO 17
<211> LENGTH: 35
<212> TYPE: DNA
<213> ORGANISM: Human immunodeficiency virus

<400> SEQUENCE: 17
tagtgcccga gcactacgtt agccaccata cggat                         35

<210> SEQ ID NO 18
<211> LENGTH: 30
<212> TYPE: DNA
<213> ORGANISM: Human immunodeficiency virus

<400> SEQUENCE: 18
tagtgcccga gcactagcca ccatacggat                               30

<210> SEQ ID NO 19
<211> LENGTH: 40
<212> TYPE: DNA
<213> ORGANISM: Human immunodeficiency virus

<400> SEQUENCE: 19
tagtgctcgg gcactgaaag acgttagcca ccatacggat                    40

<210> SEQ ID NO 20
<211> LENGTH: 43
<212> TYPE: DNA
<213> ORGANISM: Human immunodeficiency virus

<400> SEQUENCE: 20
ggttggctcg aggttggtga aagacgttag ccaccatacg gat                43

PROBES AND METHODS FOR DETECTION OF NUCLEIC ACIDS

This is a division of U.S. patent application Ser. No. 09/590,061, filed Jun. 8, 2000 now U.S. Pat. No. 6,316,200.

FIELD OF THE INVENTION

The invention relates to materials and methods for detecting nucleic acid target sequences.

BACKGROUND OF THE INVENTION

Sequence-specific hybridization of labeled oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) rather than direct detection of fluorescence intensity for detection of probe hybridization. Fluorescence energy transfer occurs between a donor fluorophore and a quencher dye (which may or may not be a fluorophore) when the absorption spectrum of one (the quencher) overlaps the emission spectrum of the other (the donor) and the two dyes are in close proximity. Dyes with these properties are referred to as donor/quencher dye pairs or energy transfer dye pairs. The excited-state energy of the donor fluorophore is transferred by a resonance dipole-induced dipole interaction to the neighboring quencher. This results in quenching of donor fluorescence. In some cases, if the quencher (also referred to as an "acceptor") is also a fluorophore, the intensity of its fluorescence may be enhanced. The efficiency of energy transfer is highly dependent on the distance between the donor and quencher, and equations predicting these relationships have been developed by Förster (1948. *Ann. Phys.* 2, 55–75). The distance between donor and quencher dyes at which energy transfer efficiency is 50% is referred to as the Förster distance ($R_0$). Other mechanisms of fluorescence quenching are also known including, for example, charge transfer and collisional quenching. In these cases the quencher may be a fluorescent dye but it need not be. Fluorescence quenching mechanisms that are not based on FET typically do not require appreciable overlap between the absorption spectrum of the quencher and the emission spectrum of the donor fluorophore.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Typically, FET and related methods have relied upon monitoring a change in the fluorescence properties of one or both dye labels when they are brought together by the hybridization of two complementary oligonucleotides. In this format, the change in fluorescence properties may be measured as a change in the amount of energy transfer or as a change in the amount of fluorescence quenching, typically indicated as an increase in the fluorescence intensity of one of the dyes. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the quencher. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352). Alternatively, the donor and quencher may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer/quenching are decreased when the oligonucleotide is hybridized. For example, an oligonucleotide labeled with donor and quencher dyes may contain self-complementary sequences that base-pair to form a hairpin which brings the two dyes into close spatial proximity where energy transfer and quenching can occur. Hybridization of this oligonucleotide to its complementary sequence in a second oligonucleotide disrupts the hairpin and increases the distance between the two dyes, thus reducing quenching. See Tyagi and Kramer (1996. *Nature Biotech.* 14, 303–308) and B. Bagwell, et al. (1994. *Nucl. Acids Res.* 22, 2424–2425; U.S. Pat. No. 5,607,834). Homogeneous methods employing energy transfer or other mechanisms of fluorescence quenching for detection of nucleic acid amplification have also been described. L. G. Lee, et al. (1993. *Nuc. Acids Res.* 21, 3761–3766) disclose a real-time detection method in which a doubly-labeled detector probe is cleaved in a target amplification-specific manner during PCR. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved.

Signal primers (sometimes also referred to as detector probes) which hybridize to the target sequence downstream of the hybridization site of the amplification primers have been described for homogeneous detection of nucleic acid amplification (U.S. Pat. No. 5,547,861 which is incorporated herein by reference). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. Examples of homogeneous detection methods for use with single-stranded signal primers are described in U.S. Pat. No. 5,550,025 (incorporation of lipophilic dyes and restriction sites) and U.S. Pat. No. 5,593,867 (fluorescence polarization detection). More recently signal primers have been adapted for detection of nucleic acid targets using FET methods which employ unfolding of secondary structures (e.g., U.S. Pat. Nos. 5,691,145 and 5,928,869). Partially single-stranded, partially double-stranded signal primers labeled with donor/quencher dye pairs have also recently been described. For example, U.S. Pat. No. 5,846,726 discloses signal primers with donor/quencher dye pairs flanking a single-stranded restriction endonuclease recognition site. In the presence of the target, the restriction site becomes double-stranded and cleavable by the restriction endonuclease. Cleavage separates the dye pair and decreases donor quenching.

U.S. Pat. No. 5,866,336 describes use of a fluorescently labeled hairpin on an amplification primer in PCR. The 3' end of the hairpin primer hybridizes to the complement of a non-target sequence appended to the target by a second primer. In this system, the hairpin primer plays an integral part in amplification of the target sequence and must be extendible. In contrast, in the present invention it is not necessary for the reporter probe to be extendible, as it does not participate in amplification of the target sequence but generates signal in a separate series of reaction steps which occur concurrently with target amplification. In further contrast, the signal primers of the invention hybridize to an internal sequence of the target (i.e., between the amplification primers), so that the signal generation reaction detects a subsequence of the target, not the amplification product itself.

Other fluorescence quenching methods for detection of a target sequence employ cleavage of a restriction site produced by direct hybridization of a probe containing the single-stranded restriction site to the single-stranded target. Japanese Patent No. 93015439 B discloses methods for measuring polynucleotides by hybridizing the single-stranded target to a single-stranded polynucleotide probe tagged with two labels which form an energy transfer pair. The double-stranded hybrid is cleaved between the labels by a restriction enzyme and fluorescence of one of the labels is measured. A disadvantage of this method is that the restriction site in the probe must also be present in the target sequence being detected. S. S. Ghosh, et al. (1994. *Nucl. Acids Res.* 22, 3155–3159) describe restriction enzyme catalyzed cleavage of fluorophore-labeled oligonucleotides which are analyzed using fluorescence resonance energy transfer. In these assays, the complementary oligonucleotides are hybridized to produce the double-stranded restriction site, with one of the fluorescent labels linked to each of the two strands.

SUMMARY OF THE INVENTION

The present invention employs a signal primer for detection of nucleic acid target sequence amplification. The signal primer of the invention is similar in structure to the signal primer described in U.S. Pat. No. 5,547,861 (which is incorporated by reference herein) but it is unlabeled. The detection system further comprises a labeled reporter probe, the 3' end of which hybridizes to the complement of the 5' tail sequence of the signal primer to produce a 5' overhang. The region of the reporter probe which forms the 5' overhang (the reporter moiety) comprises a structure or sequence which is labeled in a manner which permits detection of synthesis of the complement of the overhang. Preferably, the reporter moiety is fluorescently labeled such that fluorescence is quenched prior to extension of the signal primer and synthesis of a complementary strand. The presence of the complement of the reporter moiety, rendering it double-stranded, reduces fluorescence quenching directly and/or allows a subsequent reaction to take place to reduce quenching. In either mechanism, the complement of the labeled structure or sequence leads to an increased distance between the dyes. An associated increase in donor fluorescence or a change in another fluorescence parameter associated with decreased fluorescence quenching can be detected as an indication of amplification of the target sequence.

The 5' tail sequence of the signal primer comprises a sequence which does not hybridize to the target (the adapter sequence). The adapter sequence may be selected such that it is the same in a variety of signal primers which have different 3' target binding sequences (i.e., a "universal" 5' tail sequence). This allows a single reporter probe sequence to be used for detection of any desired target sequence, which is an advantage in that synthesis of the reporter probe is more complex due to the labeling. Further, the invention simplifies the synthesis of the target-specific signal primer. As the signal primer is not labeled, signal primers with different target binding sequences specific for different targets may be more easily and efficiently synthesized.

DETAILED DESCRIPTION OF THE INVENTION

Certain terms used herein are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described in U.S. Pat. Nos. 5,455,166; 5,270,184 and EP 0 684 315. As no special sequences or structures are required to drive the amplification reaction, amplification primers for PCR may consist only of target binding sequences. Amplification primers for 3SR and NASBA, in contrast comprise an RNA polymerase promoter near the 5' end. The promoter is appended to the target sequence and serves to drive the amplification reaction by directing transcription of multiple RNA copies of the target.

Extension products are nucleic acids which comprise a primer or a portion of a primer and a newly synthesized strand which is the complement of the sequence downstream of the primer binding site. Extension products result from hybridization of a primer to a template containing a complementary sequence and extension of the primer by polymerase using the template.

The terms target or target sequence refer to nucleic acid sequences to be amplified or detected. These include the original nucleic acid sequence to be amplified, its complementary second strand and either strand of a copy of the original sequence which is produced by replication or amplification. A target sequence may also be referred to as a template for extension of hybridized primers.

A signal primer according to the present invention comprises a 3' target binding sequence which hybridizes to a complementary sequence in the target and further comprises a 5' tail sequence which is not complementary to the target (the adapter sequence). The adapter sequence is selected such that its complementary sequence will hybridize to the 3' end of the reporter probe described below. In some embodiments of the invention the adapter sequence is selected such that its complementary sequence binds to both the 3' end of the reporter probe and to a sequence within the reporter moiety of the reporter probe, as described below. In preferred embodiments of the invention, the signal primer does not comprise a detectable label.

A reporter probe according to the present invention comprises a label which is preferably at least one donor/ quencher dye pair, i.e., a fluorescent donor dye and a quencher for the donor fluorophore. The label is linked to a sequence or structure in the reporter probe (the reporter moiety) which does not hybridize directly to the target sequence. The sequence of the reporter probe 3' to the reporter moiety is selected to hybridize to the complement of the signal primer adapter sequence. In general, the 3' end of the reporter probe does not contain sequences with any significant complementarity to the target sequence. In some instances, however, the reporter probe may contain the sequence that hybridizes to the adapter complement and another short sequence at the 3' end that hybridizes to a short segment of the target complement. In this case, the region of target complementarity is not large enough to permit significant hybridization without concurrent hybridization of the adapter-specific region of the reporter probe. The label of the reporter probe is detected as an indication of the presence of a complement of the reporter moiety which renders it double-stranded, thereby indicating the presence of or the amplification of the target. The 3' terminus of the reporter probe may be capped to prevent extension by polymerase or it may be extendible. Capping may enhance performance by reducing background signal and the nonproductive consumption of reagents in spurious side-reactions resulting from the formation of primer dimers and other errant priming events.

Any nucleic acid sequence or structure which can be labeled such that the presence of its complement, generated according to the methods of the invention, indicates the presence of the target sequence can serve as the reporter moiety of the reporter probe. Preferably, the reporter moiety is labeled with a donor/quencher dye pair such that donor fluorescence is quenched prior to detection of a target and such that quenching of donor fluorescence is reduced as an indication of the presence of the target. The reporter moiety may be a secondary structure at the 5' end of the reporter probe, such as a stem-loop (or hairpin) as described in U.S. Pat. No. 5,928,869 or a G-quartet as described in U.S. Pat. No. 5,691,145. The secondary structure is labeled such that the donor and quencher are in close proximity when the secondary structure is folded, resulting in quenching of donor fluorescence. In the presence of target, the secondary structure is unfolded in a target-dependent primer extension reaction so that the distance between the donor and quencher is increased. This decreases quenching and produces an increase in donor fluorescence which can be detected as an indication of the presence of the target sequence. Alternatively, the reporter moiety may be a single-stranded sequence at the 5' end of the reporter probe which is labeled with the donor and quencher in sufficiently close proximity to produce quenching and which contains a single-stranded restriction endonuclease recognition site (RERS) as described in U.S. Pat. Nos. 5,846,726 and 5,919,630. In the single-stranded reporter probe, the RERS is not cleavable. However, in the presence of target, the single-stranded RERS is converted to double-stranded form in a target-dependent primer extension reaction and thereby becomes cleavable. Treatment with the appropriate restriction endonuclease cleaves the RERS between the two dyes, separating them into separate nucleic acid fragments. The associated increase in distance between the dyes results in reduced quenching of donor fluorescence which can be detected as an indication of the presence of the target sequence. In a further embodiment, an RERS reporter moiety may be rendered nickable in the target-dependent primer extension reaction, as taught in U.S. Pat. Nos. 5,846,726 and 5,919,630. In this embodiment, when the RERS is rendered double-stranded the restriction endonuclease nicks the strand to which the donor and quencher are linked. Polymerase extends from the nick, displacing from the reporter probe a single-stranded fragment linked to one of the dyes. This also increases the distance between the donor and quencher and results in an increase in donor fluorescence due to decreased quenching.

Figure 1A:
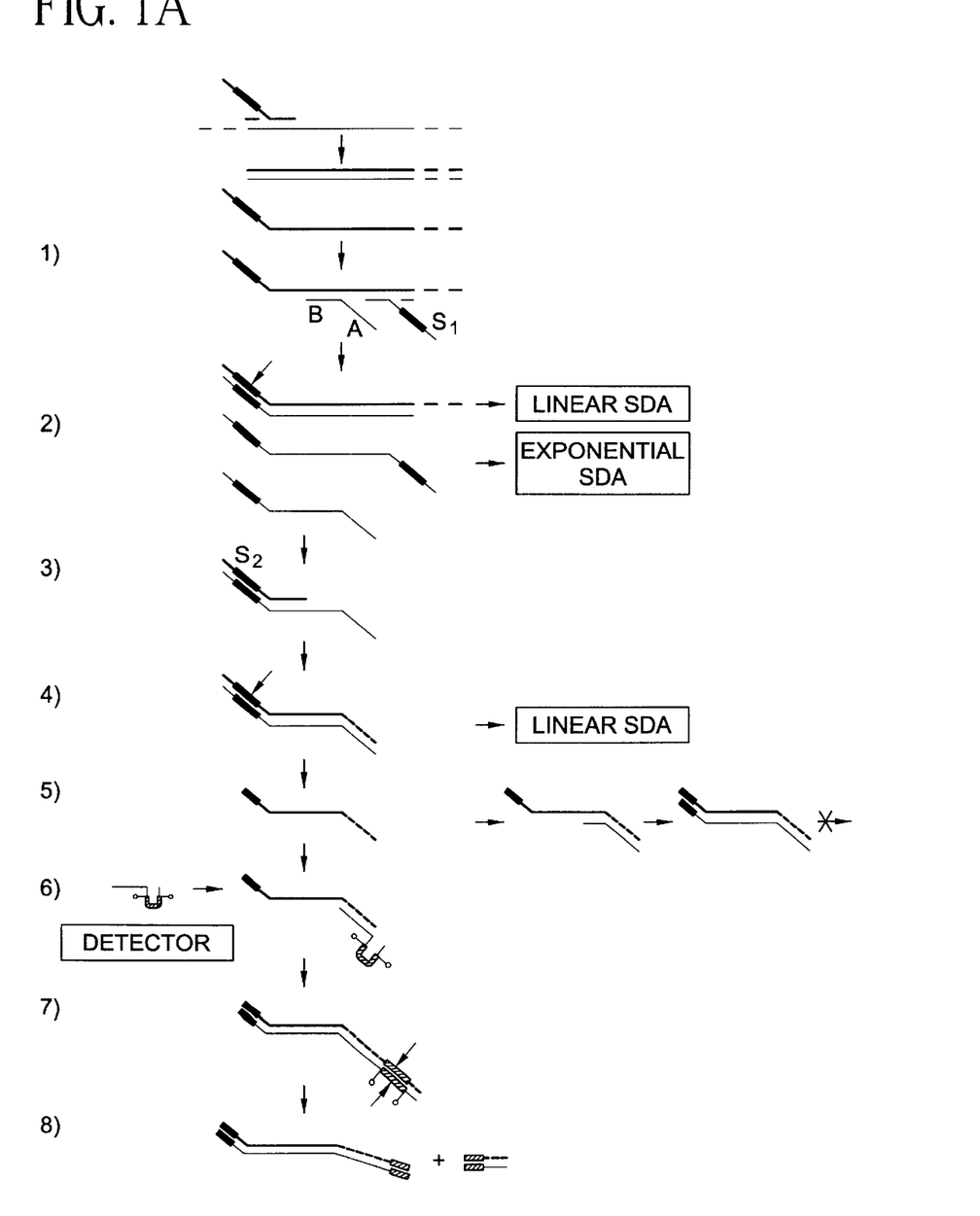
FIG. 1A illustrates detection of a nucleic acid target sequence in a Strand Displacement Amplification (SDA) reaction according to the method of the invention.

One embodiment of the method of the invention as applied to SDA is illustrated schematically in FIG. 1A. The initial steps of the reaction correspond to the signal primer reaction described in U.S. Pat. No. 5,547,861. A signal primer having a 3' target binding sequence (B) and a noncomplementary 5' tail (A) hybridizes to the target downstream from an amplification primer ($S_1$) (Step 1). As illustrated, the entire hybridization site of the signal primer is downstream from the hybridization site of the amplification primer. However, the hybridization sites of the signal primer and the amplification primer on the target may also partially overlap (typically only by several nulceotides) without significantly affecting the methods of the invention. As used herein, the term "downstream from" with respect to the hybridization sites of the signal primer and the amplification primer on the target is intended to encompass nonoverlapping and partially overlapping sites in the target. Following hybridization to the target, the amplification primer and the signal primer are simultaneously extended on the target sequence, and extension of the amplification primer displaces the single-stranded signal primer extension product (Step 2). The second amplification primer ($S_2$) hybridizes to the signal primer extension product (Step 3) and both the signal primer extension product and the amplification primer are extended to produce a double-stranded secondary amplification product with a hemimodified RERS at one end (Step 4). In SDA, nicking of the unmodified $S_2$ strand of the RERS (shown as an arrow in Step 4) and displacement of the strand downstream from the nick produces a single-stranded oligonucleotide which comprises the complement of the signal primer (Step 5). The complement of the signal primer and the double-stranded secondary amplification product are produced only when the target is present and amplified. They may therefore be detected as an indication of target amplification.

In the detection method taught in U.S. Pat. No. 5,547,861, the double-stranded secondary amplification product is detected. In contrast, the present invention detects the single-stranded oligonucleotide which is displaced from the double-stranded secondary amplification product after nicking. As this oligonucleotide comprises the complement of the signal primer, the 3' end of the reporter probe hybridizes to it (Step 6). The 5' end of the reporter probe, containing the labeled structure or sequence, forms an overhang with two recessed 3' ends which are appropriate substrates for polymerase. If the reporter probe is not capped to prevent extension, both the reporter probe and the single-stranded oligonucleotide are extended to produce a completely double-stranded molecule (Step 7). If the reporter probe is not extendible, only the recessed 3' end of the single-stranded oligonucleotide (which comprises the complement of the signal primer) is extended and the product is partially single-stranded and partially double-stranded. In either case, the sequence complementary to the labeled structure or sequence of the reporter probe is synthesized, rendering it double-stranded FIG. 1A exemplifies the invention using a hairpin reporter moiety labeled with a donor/quencher dye pair such that donor fluorescence is quenched. It will be appreciated from this example that it may not be necessary for the reporter moiety to be rendered entirely double-stranded to be detected. For example, a partial complement of the hairpin structure can be sufficient to keep the arms of the stem from hybridizing to each other. As used herein, "double-stranded reporter moiety" is intended to encompass both fully and partially double-stranded reporter moieties provided they are sufficiently double-stranded to render the reporter moiety detectable. When the reporter moiety is rendered double-stranded in the primer extension reaction, the hairpin is unfolded. Upon unfolding, the two dyes become sufficiently spatially separated to reduce or eliminate quenching of donor fluorescence by the quencher. The resulting increase in donor fluorescence, or a change in another fluorescence parameter associated with a change in fluorescence quenching (such as fluorescence lifetime, fluorescence polarization or a change in emission of the quencher/acceptor dye), may be detected as an indication of amplification of the target sequence. In addition, as illustrated in FIG. 1A, multiple reporter moieties may be combined in a single reporter probe, for example a labeled hairpin may comprise a single-stranded RERS in the single-stranded "loop." In this embodiment synthesis of the complement of the reporter moiety not only unfolds the hairpin to produce an increase in fluorescence, the RERS concurrently becomes cleavable or nickable, generally producing an additional fluorescence increase.

As depicted in FIG. 1A, the folded reporter moiety (e.g., a hairpin) of the reporter probe does not hybridize to the complement of the adapter sequence. However, the adapter sequence may be selected so that its complementary sequence will hybridize to all or part of a folded reporter moiety of the reporter probe. In this case, hybridization alone will unfold or partially unfold the reporter moiety producing signal without the need for polymerase-catalyzed extension following hybridization. The folded reporter moiety in this embodiment may comprise all or part of the reporter probe sequence. In an example of such an embodiment, the reporter probe may be a molecular beacon as described by Tyagi and Kramer, supra, in which the loop of the beacon hairpin comprises all or part of the adapter sequence. As the complement of the adapter sequence is synthesized during target amplification, it binds to the molecular beacon and unfolds the structure, producing increased fluorescence. In another embodiment the reporter probe contains a single-stranded sequence 3' to the folded reporter moiety such that both the single-stranded sequence and all or part of the folded reporter moiety hybridize to the sequence complementary to the adapter sequence as it is produced during amplification.

Figure 1B:
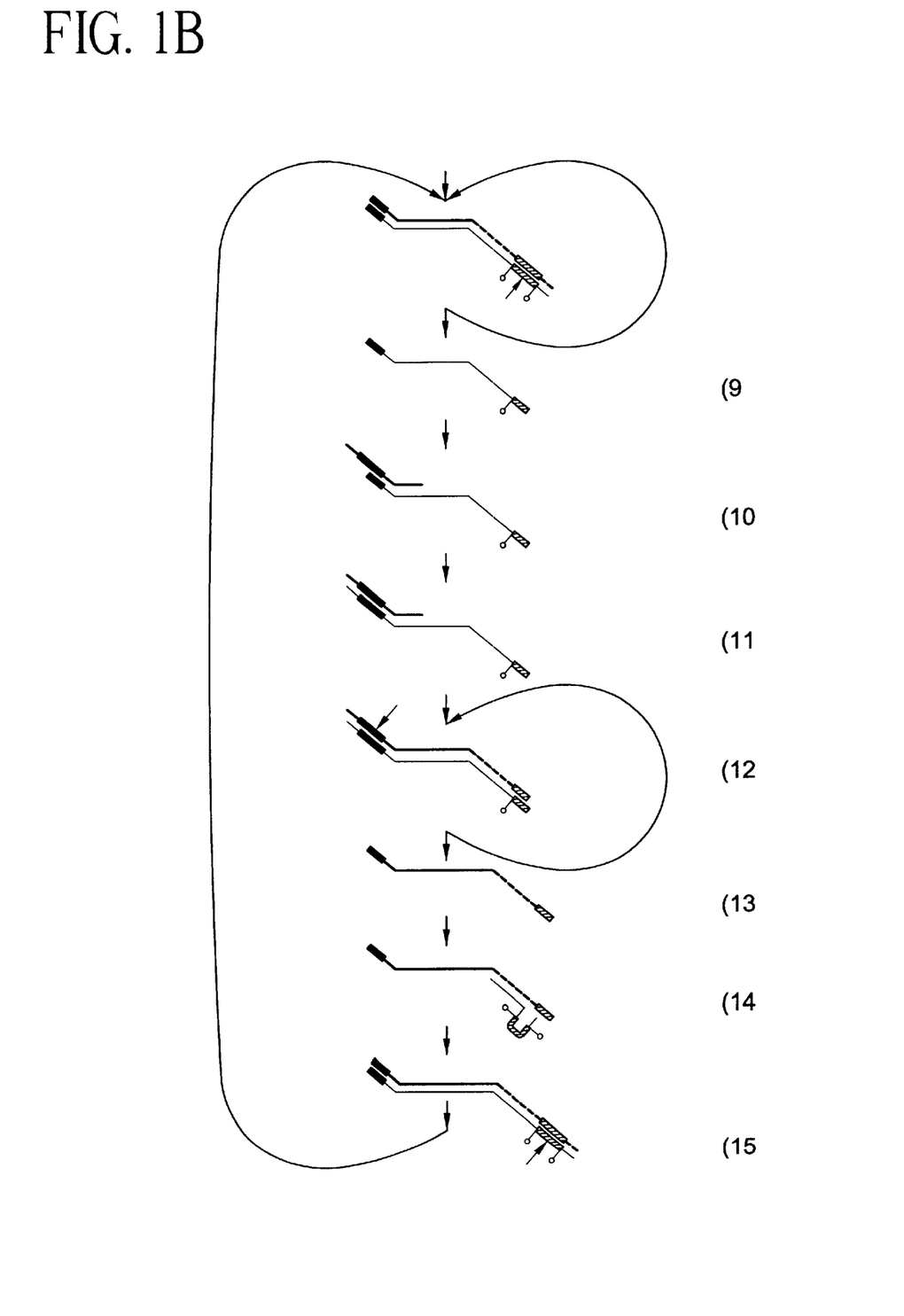
FIG. 1B illustrates the additional reaction steps which may occur when the fluorescently labeled sequence in the reporter probe is a nickable RERS.

In other alternative embodiments, other reporter moieties may be substituted in the reaction scheme shown in FIG. 1A. For example, other folded nucleic acid structures such as G-quartets may be substituted and unfolded in a similar target-dependent manner to reduce fluorescence quenching. Alternatively, a specialized linear sequence may be used as the reporter moiety, for example an RERS. When an RERS is used as the reporter moiety the donor and quencher are linked flanking the cleavage site so that when the RERS is rendered double-stranded and cleaved in a target-dependent manner the two dyes are separated onto separate nucleic acid fragments (Step 8, FIG. 1A). These alternative secondary structures may also be combined with specialized sequences, such as an RERS in a G-quartet The RERS may alternatively be rendered nickable rather than cleavable in its double-stranded form. This is a particularly suitable embodiment for use in SDA, as incorporation of modified nucleotides and production of nickable RERS's are an integral part of the amplification reaction. Generation of a nickable RERS in the reporter probe adds some additional side reactions to the reaction scheme of FIG. 1A (shown in FIG. 1B). FIG. 1B illustrates the reaction if the RERS of the double-stranded molecule illustrated in Step 7 of FIG. 1A is nicked rather than cleaved. Referring to FIG. 1B, as polymerase extends from the nick two products are produced: the double-stranded molecule is regenerated (now carrying only one of the two dyes) and the single-stranded molecule downstream from the nick is displaced (Step 9, carrying the other of the two dyes). The double-stranded molecule can be renicked with displacement of additional single-stranded molecules and the displaced single-stranded molecules hybridize to an amplification primer (Step 10) and be extended to produce a nickable RERS in a fully double-stranded molecule (Steps 11 and 12). Further nicking and displacement produces single-stranded molecules with a partial RERS derived from the previous reporter probe at one end and no label (Step 13). This hybridizes to a new reporter probe (Step 14) and the recessed end becomes extendible as the hairpin breathes and allows the partial RERS to hybridize. Filling-in of the recessed end renders the RERS nickable (Step 15) and the displaced single-stranded molecule re-enters the reaction and the cycle repeats. This amplifies the signal initially produced from a single signal primer/target interaction by means of a separate reaction occurring independently of any further target amplification.

In general, the length of the sequences involved in intermolecular base-pairing between the complement of the adapter sequence of the signal primer and the reporter probe is not critical. For the signal primer, however, it has been observed that in general the $T_m$ of the target binding sequence has a greater influence on assay efficiency and that longer target binding sequences generally produce more fluorescent signal in the assay. This may be due to the competition between the signal primer and the extension product of the upstream amplification primer for hybridization to the target sequence. The appropriate length for the signal primer and the reporter probe is determined by the number of nucleotides required for stable base-pairing to maintain a partially double-stranded molecule under the selected reaction conditions and is within the ordinary skill in the art. For convenience, the sequences involved in base-pairing are typically between about 8 and 75 nucleotides in length. The maximum length is limited only by practical concerns such as the ease and efficiency of oligonucleotide synthesis and recovery.

Selection of the appropriate concentrations of signal primer and reporter probe in the reaction is also within the ordinary skill in the art. Preferably the concentration of signal primer and reporter probe is relatively high and the concentration of upstream amplification primer is relatively low, as this generally provides higher fluorescent signal generation in the reaction.

A second signal primer which hybridizes to the second, complementary strand of a double-stranded target sequence may optionally be included in the reaction provided that the first and second signal primers do not hybridize to each other. The second signal primer hybridizes to the second strand of the target sequence downstream of the second amplification primer and is extended and displaced by extension of the second amplification primer. The second signal primer extension product is rendered double-stranded by hybridization and extension of the first amplification primer. Generation of the double-stranded labeled structure or sequence and separation of the dye pair proceed as for the first strand of the target sequence. The second signal primer preferably comprises the same 5' adapter sequence as the first signal primer to allow detection of the products of amplification of both target strands with a single reporter probe.

In addition, multiple signal primers per strand of target may be employed if desired, each hybridizing to the target sequence downstream of the other on the same strand, with all signal primers being hybridized downstream of the amplification primer. In this manner, each signal primer is displaced by extension of the upstream detector nucleic acid and the most 5' signal primer is displaced by the amplification primer. Use of multiple signal primers has the advantage of increasing or amplifying the signal generated per target, with an increase in sensitivity of the assay. Again, it is preferable, but not necessary, that all of the signal primers comprise the same 5' adapter sequence to allow detection of all reaction products using a single reporter probe.

Multiple signal primers may also be used to simultaneously detect a plurality of different target sequences. In this case, the 5' adapter sequences of the signal primers are preferably different for each target to be detected. By labeling reporter probes specific for the 5' adapter sequence of each target-specific signal primer with donor/quencher dye pairs which are distinguishable, the presence of each target may be determined by detecting changes in the extent of fluorescence quenching in the reporter probe directed to each target. This embodiment of the invention is particularly useful for detection of single nucleotide sequence variations such as are associated with certain disease states and conditions. The target binding sequence of each signal primer may be selected to be specific for a specific sequence variant of the target. Only those signal primers which comprise the correct target binding sequence for hybridization to the target will hybridize, be extended and result in a complement of the adapter sequence being produced. The reporter probe specific for that adapter sequence complement will then produce a signal indicating which sequence variant(s) is/are present by virtue of its distinguishing label.

Alternatively, for separate assay of multiple different targets, the same 5' adapter sequence may be used in signal primers directed to the multiple different target sequences. Specificity for the different target sequences is conferred by varying the 3' target binding sequence of the signal primer. This approach not only simplifies the design and synthesis of signal primers, it allows the same reporter probe to be used to detect any desired target sequence. Commercially, this has the advantage that production of only a single reporter probe is necessary to produce assay systems for a variety of targets, thus lowering production costs and simplifying the development of assays for new targets. Further, synthesis of the various signal primers is simplified and less expensive because they do not require labeling.

It will be apparent that, in addition to SDA, the signal primers of the invention may be adapted for use in other primer extension amplification methods (e.g., PCR, 3SR, TMA or NASBA). For example, the methods may be adapted for use in PCR by substituting PCR amplification primers and employing a strand displacing DNA polymerase which lacks 5'→3' exonuclease activity (e.g., Sequencing Grade Taq from Promega or exo⁻ Vent or exo⁻ Deep Vent from New England BioLabs) in the PCR. The signal primers hybridize to the target downstream from the PCR amplification primers. They are extended, displaced from the target and rendered double-stranded essentially as described for SDA. The single-stranded oligonucleotide comprising the complement of the signal primer 5' adapter sequence is generated by denaturing the double-stranded secondary amplification product, followed by hybridization of the reporter probe and polymerase extension to synthesize the complementary strand of the labeled reporter moiety in the reporter probe. As in SDA systems, synthesis of the complementary strand either directly or indirectly provides a change in the proximity of donor and quencher dyes and changes the degree of fluorescence quenching. An associated change in a fluorescence parameter, such as intensity, serves as an indication of target amplification.

For adaptation of the inventive methods to 3SR, TMA or NASBA, a 5'→3' exonuclease deficient reverse transcriptase with strand displacing activity is employed, with hybridization of the signal primer to the RNA target downstream of an amplification primer. In a reaction scheme similar to that previously described, the hybridized signal primer is 1) extended, and 2) displaced by extension of the upstream amplification primer. The displaced signal primer extension product is then made entirely double-stranded by hybridization and extension of the second amplification primer which contains an RNA polymerase promoter. The promoter sequence, which is located on the 5' tail of the second amplification primer, is made double-stranded by extension of the 3' end of the signal primer extension product. From the double-stranded promoter, RNA polymerase generates RNA copies complementary to the signal primer extension product. The 3' end of each RNA copy contains a sequence complementary to the adapter sequence of the signal primer. This sequence then hybridizes to a complementary region of the reporter probe. If the reporter probe is extendible, reverse transcriptase will extend the 3' end of the probe upon the RNA template to produce a reporter probe extension product. RNase H will then degrade the RNA strand of this heteroduplex, freeing the reporter probe extension product to hybridize with the second amplification primer containing the promoter sequence. Conversion of the promoter sequence to the double-stranded form will initiate a new round of RNA synthesis, yielding products that are complementary to the reporter probe extension product, including the full reporter moiety sequence. Hybridization of reporter probes to these RNA targets will cause the reporter moiety to unfold, producing signal as donor and quencher dyes are separated and quenching is reduced. In addition, the reporter probes will be extended upon the RNA target as described above and the cycle will be repeated.

If the reporter probes are not extendible (capped) the adapter sequence of the signal primer must be selected to contain sequences such that the complement of the adapter sequence will hybridize to the reporter moiety of the reporter probe. The reaction will proceed as described above, except that the capped reporter probes will not be extended and the RNA complements of the signal primer extension product will hybridize to the capped reporter probe (including the reporter moiety). Signal will be produced as the reporter moiety unfolds and quenching of donor fluorescence is relieved during hybridization.

For reduced background, it is preferred that the signal primers of the invention be used as described above, with the signal primer extension product being separated from the target sequence by displacement due to extension of the upstream amplification primer. However, it will be apparent that the amplification primers known for use in the various nucleic acid amplification reactions may themselves be used for hybridization of the reporter probe if the primers contain appropriate adapter sequences. In this embodiment, the adapter sequence of an SDA primer is located between the nickable restriction endonuclease site that drives SDA and the target binding sequence. SDA with this primer will produce an amplified product that contains at its 3' end a sequence complementary to the reporter probe. Binding of the reporter probe to this complementary sequence will produce signal as described above. For PCR and NASBA the amplification primers are modified by addition of a non-complementary 5' tail as described above for the signal primer. In the case of NASBA, the primer lacking the RNA polymerase promoter is the primer modified with the 5' adapter sequence. During PCR and NASBA, complements of the adapter-containing primer extension products are produced as described above for the signal primers. These complementary sequences are made single-stranded either by heat denaturation (PCR) or enzymatic digestion of RNA template (RNase H in NASBA), and the single-stranded complement then binds to reporter probe as described above for signal primers. The use of amplification primers as signal primers eliminates the need for the additional signal primer in the reaction, but because background may be higher in this embodiment the sensitivity of the assay may be decreased.

In other alternative embodiments, the signal primers of the invention may be used in non-amplification based assay formats to detect target sequences. In a first non-target amplification embodiment, the 3' single-stranded target binding sequence of the signal primer hybridizes to the 3' end of the target sequence such that the 5' adapter sequence forms a 5' overhang. The target sequence functions as a primer for synthesis of a strand complementary to the signal primer using a polymerase to extend the target sequence using the 5' overhang as a template. If the target binding sequence of the signal primer hybridizes to only a portion of the target sequence, the target sequence also forms a 5' overhang and the signal primer may be similarly extended using the 5' overhang of the target as a template. Alternatively, the signal primer may be non-extendible as synthesis of a copy of the target sequence is not required in this embodiment of the invention. In either case, the complement of the adapter sequence of the signal primer is synthesized. Upon separation of the two strands, the complement of the signal primer adapter sequence in the target will hybridize to the 3' end of the reporter probe, rendering the labeled reporter moiety double-stranded upon polymerase extension of the recessed 3' end of the adapter sequence complement. An advantage of this embodiment over the reaction described in U.S. Pat. No. 5,866,336 is that use of the overhang allows synthesis of the complement of the adapter sequence in a single extension step rather than two. That is, the complement of the adapter sequence is appended directly to the original target, thus allowing target detection without requiring amplification. In a second preferred non-target amplification embodiment of the invention the signal primer is hybridized to an internal sequence of the target with an additional primer hybridized upstream to displace it (commonly referred to as a "bumper" primer). The signal primer and bumper primer are extended such that the signal primer extension product is displaced from the target sequence. A second pair of primers are hybridized to the extension product and extended such that the downstream primer extension product contains the complement of the adapter sequence and is displaced from the signal primer extension product by extension of its bumper primer. The reporter probe hybridizes to the complement of the adapter sequence and the adapter sequence is extended as described herein to synthesize the complement of the reporter moiety. Because this is an isothermal reaction which depends on strand displacement to separate complementary strands, extension of the first bumper primer renders the target double-stranded and unable to participate in any further reaction steps. Although a copy is generated and displaced, this is not considered target amplification because the copy represents a subsequence of the original target which is detected as an indication of the presence of the target and only one copy of the subsequence is generated per original target sequence.

The foregoing disclosure primarily relates to preferred embodiments in which the reporter moiety is labeled with a fluorescent donor/quencher dye pair and synthesis of the complement of the reporter moiety is detected by an increase in fluorescence. This label system allows synthesis of the complement to be detected in real-time and/or in a homogeneous assay (i.e., without separation of the label prior to detection). However, other labels useful in the invention will be apparent to those skilled in the art. For example, a single fluorescent label may be employed on the reporter moiety with detection of a change in fluorescence polarization in the presence of the complement of the reporter moiety (see U.S. Pat. No. 5,593,867). Non-fluorescent labels are also useful. For example, the reporter moiety may be labeled with a lipophilic dye and contain a restriction site which is cleaved in the presence of the complement of the reporter moiety (see U.S. Pat. No. 5,550,025). Alternatively, the reporter probe may be radiolabeled and the products resulting from synthesis of the complement of the reporter moiety may be resolved by electrophoresis and visualized by autoradiography. Immunological labels may also be employed. A reporter probe labeled with a hapten can be detected after synthesis of the complement of the reporter moiety by first removing unreacted reporter probe (for example by adapter-specific capture on a solid phase) and then detecting the hapten label on the reacted reporter probe using standard chemiluminescent or colorimetric ELISAs. A biotin label may be substituted for the hapten and detected using methods known in the art.

The label indicating the presence of the complement of the reporter moiety may be detected at a selected endpoint in the reaction. However, because oligonucleotides with increased distance between the donor and the quencher are produced concurrently with hybridization and primer extension, the label may also be monitored as the reaction is occurring, i.e., in "real-time". This homogeneous, real-time assay format can be used to provide semi-quantitative or quantitative information about the initial amount of target present. For example, the rate at which the label (e.g., fluorescence intensity) changes during the reaction (either as part of target amplification or in non-amplification detection methods) is an indication of initial target levels. As a result, when more initial copies of the target sequence are present, the label more rapidly reaches a selected threshold value (i.e., shorter time to positivity). In addition, the rate of change in the label during the course of the reaction is more rapid in samples containing higher initial amounts of target than in samples containing lower initial amounts of target. These or other measurements as are known in the art may be made as an indication of the presence of target or as an indication of target amplification. The initial amount of target is typically determined by comparison of the experimental results to results for known amounts of target.

Many donor/quencher dye pairs known in the art are useful in preferred embodiments of the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/ tetramethylrhodamine (TAMRA), and others. The selection of a particular donor/quencher pair is not critical. For energy transfer quenching mechanisms it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl) aminonaphthalene (EDANS). Certain donor/quencher pairs are exemplified above and in the following Examples, however, others will be apparent to those skilled in the art and are also useful in the invention. Any dye pair which produces fluorescence quenching in the reporter probes of the invention are suitable for use in the methods of the invention, regardless of the mechanism by which quenching occurs. Terminal and internal labeling methods are also known in the art and may be routinely used to link the donor and quencher dyes at their respective sites in the reporter probe.

EXAMPLE 1

Strand Displacement Amplification reactions containing signal primers according to the invention were run essentially as described in U.S. Pat. No. 5,547,861 for detection of a synthetic target sequence. A first reaction contained $10^6$ copies of the target sequence, SDA amplification primers appropriate for amplification of the synthetic target sequence, 100 nm of a signal primer according to the invention comprising a target binding sequence specific for the target and a 5' tail sequence identical to the 3' sequence of a reporter probe, and 200 nm of the reporter probe. The sequence of the reporter probe contained an RERS in the 5' region flanked by fluorescein and Rhodamine X (Rox) such that fluorescence of fluorescein was quenched when the RERS was intact. The sequences of the signal primer and reporter probe (shown in the 5' to 3' direction) are shown below. The target binding sequence is shown in italics, the 5' adapter sequence of the signal primer and the identical 3' sequence of the reporter probe are underlined and the RERS of the reporter probe is bolded.

Figure 2:
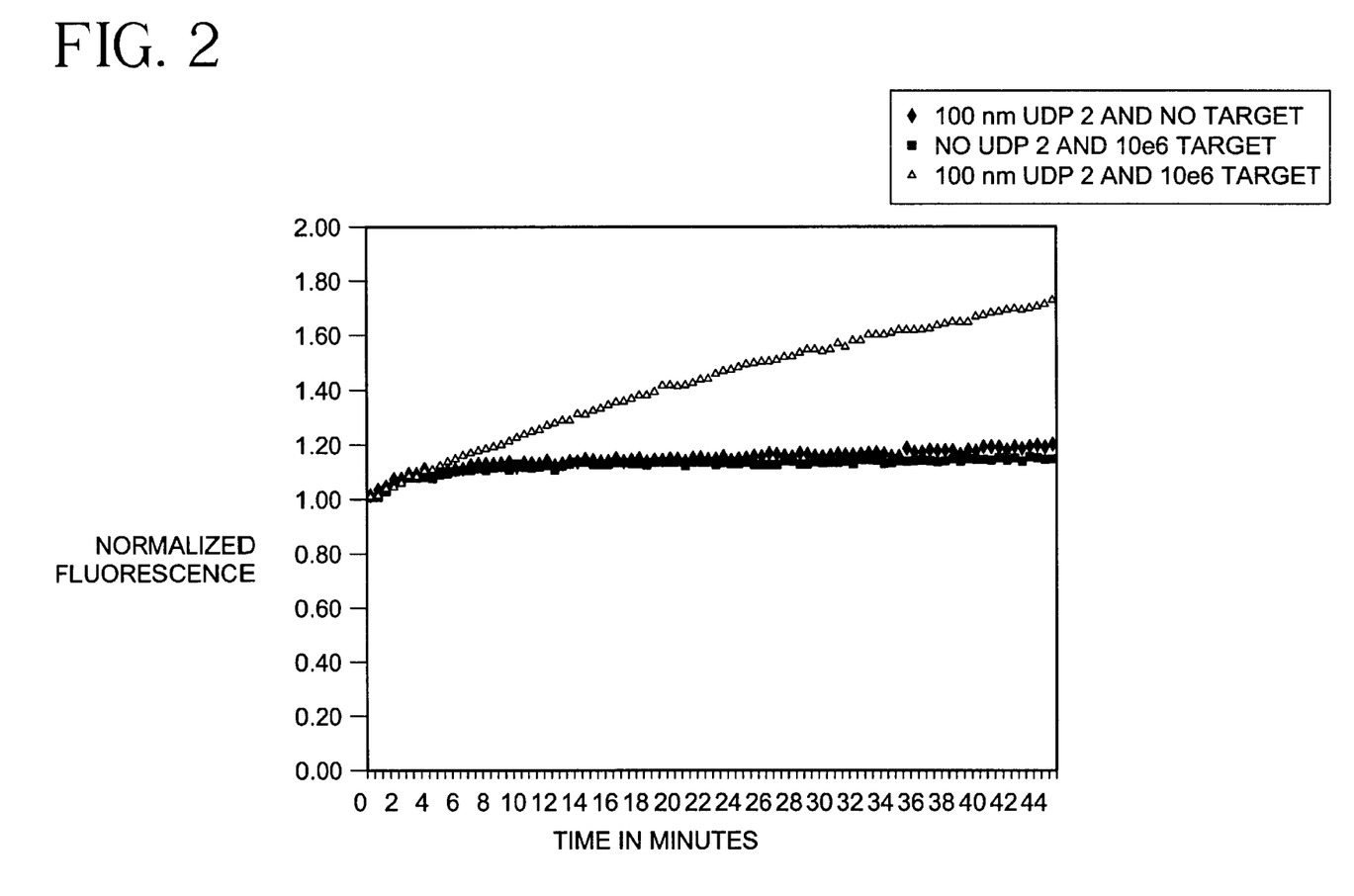
FIG. 2 illustrates the results of Example 1.

A second reaction contained no target and the same signal primer as in the first reaction. A third reaction was a control reaction which contained only $10^6$ copies of target and the reporter probe (i.e., no signal primer). Fluorescein fluorescence was detected in real-time during the amplification reactions. As shown in FIG. 2, donor fluorescence remained low and constant in the absence of target, indicating quenching of fluorescence throughout the reaction due failure of the RERS of the reporter probe to be converted to double-stranded form and cleaved. In the absence of signal primer donor fluorescence also remained quenched throughout the amplification reaction. In the presence of target, signal primer and reporter probe, however, donor fluorescence was initially low but increased during the time course of the amplification reaction as the RERS of the reporter probe was converted to double-stranded form and cleaved to reduce the extent of fluorescence quenching. These results demonstrate that the signal primers and reporter probes of the invention can be used to detect a nucleic acid target sequence by monitoring changes in the extent of fluorescence quenching.

In a similar experiment, 0 and 250 copies of cloned HIV target DNA were detected using a variety of signal primers in combination with one of two reporter probes, each having the same sequence but labeled with different donor/quencher dye pairs. The sequences of the signal primers and reporter probes are shown in the 5' to 3' direction below. The target binding sequence is shown in italics, the 5' adapter sequence of the signal primer and the identical 3' sequence of the reporter probe are underlined and the RERS of the reporter probe is bolded.

Signal Primers:

```
Signal Primer (SEQ ID NO:1):   CCAAAATGACAGCTTCTGATGGAATGACTCACTGAGTTGGAACGT Reporter Probe (SEQ ID NO:2):  (fluorescein)TACCTCGAGT(rox)GCAGCCAAAAGACAGCTTCTGATGGAA
```

| | |
|---|---|
| GAAAGACGTTAGCCACCATACGGATA*CCCCTTTTCTTTTAAAATTGTG* | (SEQ ID NO:3, UA1) |
| GAAAGACGTTAGCCACCATACGGATA*CCCCTTTTCTTTTAAAATTGTGGATG* | (SEQ ID NO:4, UA2) |
| GAAAGACGTTAGCCACCATACGGATA*CCCCTTTTCTTTTAAAATT* | (SEQ ID NO:5, UA3) |
| GAAAGACGTTAGCCACCATACGGATA*CCCCTTTTCTTTTAAAATTG* | (SEQ ID NO:6, UA3.1) |
| ACGTTAGCCACCATACGGATA*CCCCTTTTCTTTTAAAATTGTG* | (SEQ ID NO:7, UA4) |
| ACGTTAGCCACCATACGGATA*CCCCTTTTCTTTTAAAATTGTGGATG* | (SEQ ID NO:8, UA5) |
| ACGTTAGCCACCATACGGATA*CCCCTTTTCTTTTAAAATT* | (SEQ ID NO :9, UA6) |
| ACGTTAGCCACCATACGGATA*CCCCTTTTCTTTTAAAATTG* | (SEQ ID NO: 10, UA6.1) |

-continued

```
AGCCACCATACGGATACCCCTTTTCTTTTAAAATTGTG               (SEQ ID NO:11, UA7)

AGCCACCATACGGATACCCCTTTTCTTTTAAAATTGTGGATG           (SEQ ID NO:12, UA8)

AGCCACCATACGGATACCCCTTTTCTTTTAAAATT                  (SEQ ID NO:13, UA9)

AGCCACCATACGGATACCCCTTTTCTTTTAAAATTG                 (SEQ ID NO:14, UA9.1)

Reporter Probes                                      (SEQ ID NO:15)
(fluorescein)TGCCCGAGT(dabcyl)GAAAGACGTTAGCCACCATACGGAT (fluorescein)TGCCCGAGT(rox)GAAAGACGTTAGCCACCATACGGAT
```

The signal primers differed in length and $T_m$ of the target binding sequence and of the reporter binding sequence. Fluorescein fluorescence was monitored during amplification. To compare the reporter probe/signal primer combinations, results were expressed as the area under the fluorescence curve or "MOTA". The more area under the curve, the more fluorescence generated by a particular reporter probe/signal primer combination and the more efficient the detection of amplified products. Both reporter probes worked well in combination with all signal primers for detection of the HIV target, although performance was generally not as good as for reporter probes containing hairpin reporter moieties. However, linear reporter probes such as these are shorter than reporter probes containing secondary structures and are therefore easier to synthesize with higher yield. Higher MOTA values were obtained using the fluorescein-dabcyl reporter probe, suggesting that this dye pair may have a higher quenching efficiency.

longer target binding sequences performing better than those with shorter target binding sequences.

The experiment was repeated using three different reporter probes, including SEQ ID NO:16. The additional reporter probes were as follows:

```
(fluorescein)TAGTGCCCGAGCACT(dabcyl)ACGTTAGCCACCATACGGAT  (SEQ ID NO:17, TBD10)

(fluorescein)TAGTGCCCGAGCACT(dabcyl)AGCCACCATACGGAT       (SEQ ID NO:18, TBD11)
```

EXAMPLE 2

SDA reactions were prepared to contain the different signal primers shown in Example 1, either 0 or 5,000 copies of the cloned HIV target, and a reporter probe. The sequence of the reporter probe was as follows:

```
(dabcyl)TAGTGCCCGAGCACT(rox)GAAAGACGTTAGCCACCATACGGAT (SEQ ID NO:16, TBD9)
```

Figure 3A:
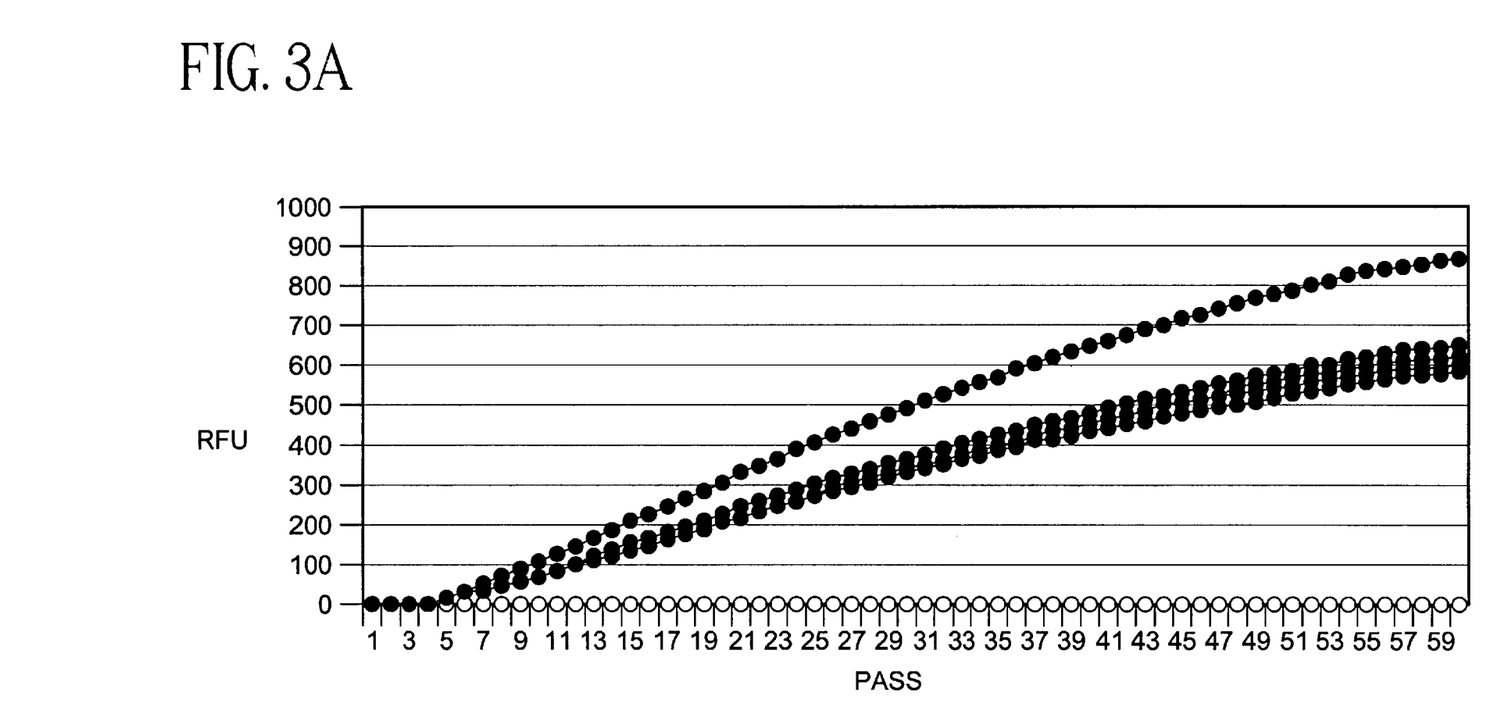
FIG. 3A and FIG. 3B illustrate the results of Example 2.
Figure 3B:
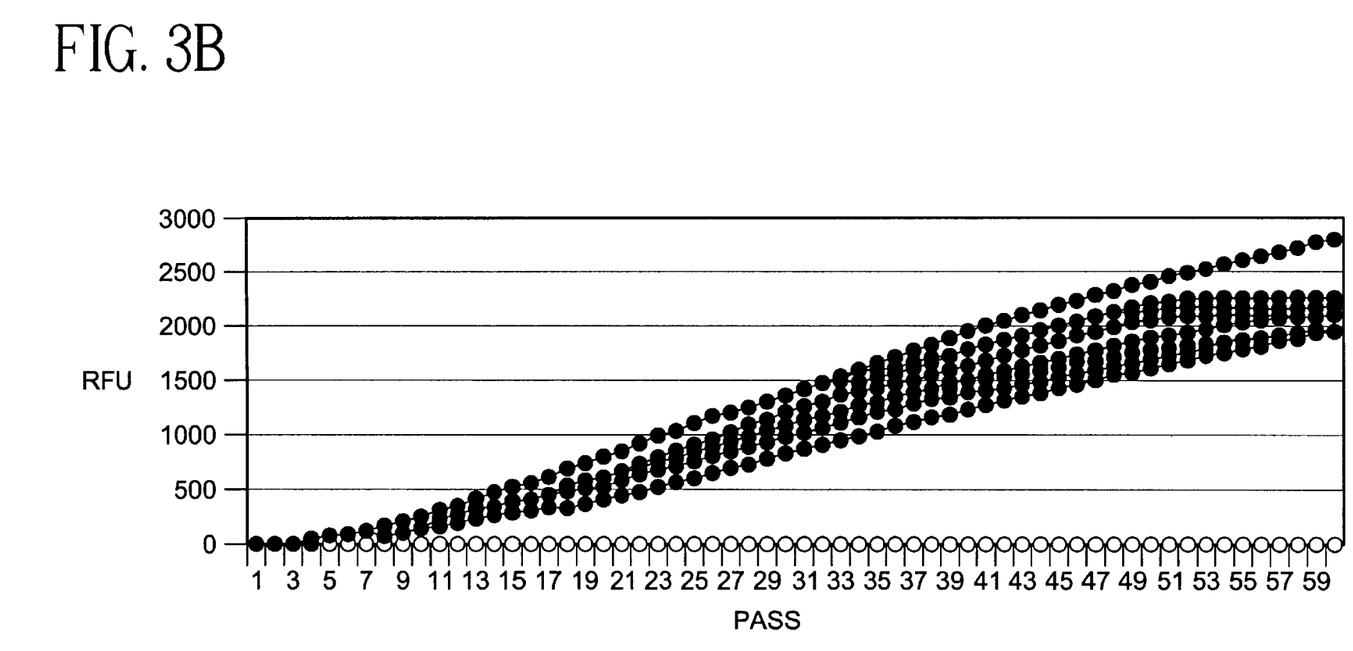

SEQ ID NO:16 contains a BsoBI RERS in the single-stranded loop of a hairpin structure at the 5' end. The SDA reactions contained 500 nm SDA amplification primers, 50 nM bumper primers, and 200 nM each signal primers and reporter probes. Rhodamine fluorescence was monitored during amplification. For each signal primer/reporter probe combination rhodamine fluorescence increased in the presence of target during the amplification reaction. In the absence of target rhodamine fluorescence remained low throughout the reaction. The results of one of the reactions are shown in FIG. 3A, for signal primer SEQ ID NO:3, with the multiple curves representing replicate samples. Results indicated that the length and $T_m$ of the adapter sequence did not significantly affect assay performance. However, the $T_m$ of the target binding sequence of the signal primer influenced signal generation, with signal primers comprising In this experiment the concentration of the upstream amplification primer was reduced to 100 nM. Amplification was performed in the presence of either 0 or 250 copies of target DNA. Reactions containing target showed a rapid increase in fluorescein fluorescence after as little as 5 min. of incubation. In contrast, reactions without target exhibited low fluorescein fluorescence throughout the reaction period. Results for a reaction containing SEQ ID NO:8 abd SEQ ID NO:17 are shown in FIG. 3B, with the multiple curves representing replicate samples. The reporter probe/signal primer combinations SEQ ID NO:16/SEQ ID NO:4 and SEQ ID NO:17/SEQ ID NO:8 produced similar MOTA values (62,147 and 66,051 respectively), whereas the SEQ ID NO:18/SEQ ID NO:12 combination was less efficient (MOTA=49,879) suggesting less efficient hybridization and conversion due to the shorter probe and primer length.

EXAMPLE 3

In this experiment a reporter probe comprising a hairpin and a nickable rather than cleavable BsoBI RERS was tested in SDA. The reporter probe had the following sequence (SEQ ID NO:19, TBD13.1):

```
(fluorescein)TAGTGCTCGGGCACT(dabcyl)GAAAGACGTTAGCCACCATACGGAT
```

This reporter probe was used with SEQ ID NO:4 as the signal primer in the amplification reaction. A mean MOTA value of 48,000 was obtained in the presence of 250 copies of HIV target DNA, compared with a score of less than 150 from negative controls. The lower MOTA score observed as compared to reporter probe SEQ ID NO:16, which has the same 3' tail sequence may be due to inefficient priming of the polymerase off the short oligonucleotide that is left after nicking of the BsoBI site. Performance of the reaction may be enhanced by increasing the length of the hairpin to stabilize this oligonucleotide and provide a larger region for binding of the polymerase.

EXAMPLE 4

In this experiment SDA was performed using a reporter probe containing a G-quartet structure and an RERS as the reporter moiety. This reporter probe had the following sequence (SEQ ID NO:20, TBD14):

(fluorescein)GGTTGGCTCGAGGTTGGT(dabcyl)GAAAGACGTTAGCCACCATACGGAT

An increase in fluorescein fluorescence was observed during the course of amplification of 250 copies of HIV target DNA. No such increase in fluorescence was observed in the absence of target.

What is claimed is:

1. A method for detecting amplification of a target sequence comprising, in an amplification reaction:
   a) hybridizing a signal primer comprising an adapter sequence to the target sequence;
   b) extending the signal primer on the target sequence to produce an extension product;
   c) separating the extension product from the target sequence;
   d) hybridizing an amplification primer to the extension product and extending the amplification primer to synthesize a complement of the adapter sequence;
   e) separating the product including the complement of the adapter sequence from the extension product;
   f) hybridizing to the complement of the adapter sequence a reporter probe comprising a reporter moiety, and producing a double-stranded reporter moiety; and
   g) detecting the double-stranded reporter moiety as an indication of amplification of the target sequence.

2. The method of claim 1 wherein the reporter is a molecular beacon.

3. The method of claim 1 wherein the double-stranded reporter moiety is produced upon synthesis of a complement of the reporter moiety.

4. The method of claim 1 wherein the target sequence is amplified by SDA, PCR, 3SR, TMA or NASBA.

5. The method of claim 1 wherein a change in fluorescence is detected.

6. The method of claim 5 wherein the change in fluorescence is detected in real-time.

7. The method of claim 5 wherein the change in fluorescence is detected at a selected end-point in the amplification reaction.

8. The method of claim 1 wherein the reporter moiety is labeled with a fluorescent donor/quencher dye pair.

9. The method of claim 1 wherein the reporter moiety is selected from the group consisting of secondary structures and specialized sequences.

10. The method of claim 9 wherein the double-stranded reporter moiety is detected by unfolding of a hairpin structure, unfolding of a G-quartet or by nicking or cleavage of a restriction endonuclease recognition site.

11. The method of claim 9 wherein a change in the fluorescence results directly from unfolding of a secondary structure.

12. The method of claim 9 wherein a change in fluorescence results from cleavage or nicking of a restriction endonuclease recognition site in the double-stranded reporter moiety.

13. The method of claim 1 wherein the reporter probe is non-extendible.

14. The method of claim 1 which comprises multiple signal primers, each signal primer having a separately detectable adapter sequence.

15. The method of claim 14 wherein each signal primer hybridizes to a different sequence variant of the target sequence.

* * * * *